United States Patent
Cavanak et al.

[11] Patent Number: 6,066,616
[45] Date of Patent: May 23, 2000

[54] SOMATOSTATIN ANALOGUE COMPOSITION AND USE IN TREATING BREAST CANCER

[75] Inventors: Thomas Cavanak, Biel-Benken; Alan Harris, Basel, both of Switzerland

[73] Assignee: Novartis AG, Basel, Switzerland

[21] Appl. No.: 09/022,079

[22] Filed: Feb. 11, 1998

Related U.S. Application Data

[62] Division of application No. 08/471,706, Jun. 6, 1995, Pat. No. 5,753,618, which is a continuation of application No. 08/301,369, Sep. 6, 1994, abandoned, which is a continuation of application No. 08/060,690, Apr. 11, 1993, abandoned, which is a continuation of application No. 07/780,188, Oct. 22, 1991, abandoned, which is a continuation of application No. 07/627,300, Dec. 14, 1990, abandoned, which is a continuation of application No. 07/217,019, Jul. 8, 1988, abandoned.

[30] Foreign Application Priority Data

Jul. 10, 1987 [GB] United Kingdom .................. 8716324
Jul. 10, 1987 [GB] United Kingdom .................. 8716326

[51] Int. Cl.[7] .................................................. A61K 38/31
[52] U.S. Cl. ............................... 514/11; 514/9; 530/317
[58] Field of Search ............................. 530/317; 514/11, 514/9

[56] References Cited

U.S. PATENT DOCUMENTS

| | | | |
|---|---|---|---|
| 4,146,612 | 3/1979 | Veber | 530/311 |
| 4,328,214 | 5/1982 | Rink et al. | 514/11 |
| 4,603,120 | 7/1986 | Kamber | 514/11 |
| 4,650,787 | 3/1987 | Schally et al. | 530/311 |
| 4,767,628 | 8/1988 | Hutchinson | 514/12 |
| 4,900,730 | 2/1990 | Miyauchi | 514/12 |
| 5,187,150 | 2/1993 | Speiser et al. | 514/12 |
| 5,384,309 | 1/1995 | Barber et al. | 514/11 |

FOREIGN PATENT DOCUMENTS

| | | |
|---|---|---|
| 84721/91 | 11/1991 | Australia . |
| 0070021 | 1/1983 | European Pat. Off. . |
| 0143307 | 6/1985 | European Pat. Off. . |
| 0203031 | 11/1986 | European Pat. Off. . |
| 0214872 | 3/1987 | European Pat. Off. . |
| 0215171 | 3/1987 | European Pat. Off. . |
| 0477885 | 4/1992 | European Pat. Off. . |
| 0621770 | 2/1981 | Switzerland . |
| 2169291 | 7/1986 | United Kingdom . |
| 8802756 | 4/1988 | WIPO . |

OTHER PUBLICATIONS

Cancer Research 47, 1566–1570, Mar. 15, 1987, Buddy Setyono–Han et al., pp. 1566–1570.
Europ. J. Cancer Vol. 27, Suppl. 2, p. S312 Abstr. No. 1920–1991.
J. Cancer Res. Clin. Oncol. Vol. 116 (Supply./Part 1), p. 466, Abstr. No. A4. 123.05–1990.
European Journal of Cancer 1991–Vol. 27, (Suppl. 2). P. S287 (Abs. 1761).
Proceedings of Asco Vol. 12 Mar. 1993–p. 93.

*Primary Examiner*—Cecilia J. Tsang
*Attorney, Agent, or Firm*—Hesna J. Pfeiffer

[57] ABSTRACT

The invention provides a pharmaceutical composition comprising a somatostatin analogue, and its use in the treatment of breast cancer. The pharmaceutical composition preferably contains lactic acid in addition to the somatostatin analogue and is better tolerated when administered by injection.

2 Claims, No Drawings

SOMATOSTATIN ANALOGUE COMPOSITION AND USE IN TREATING BREAST CANCER

This case is a division of U.S. Ser. No. 08/471,706, filed Jun. 6, 1995, now U.S. Pat. No. 5,753,618, issued May 19, 1998, which in turn was a continuation of U.S. Ser. No. 08/301,369, filed Sep. 6, 1994, now abandoned, which in turn was a continuation of U.S. Ser. No. 08/060,690, filed Apr. 11, 1993, now abandoned, which in turn was a continuation of U.S. Ser. No. 07/780,188, filed Oct. 22, 1991, now abandoned, which in turn was a continuation of U.S. Ser. No. 07/627,300, filed Dec. 14, 1990, now abandoned, which in turn was a continuation of U.S. Ser. No. 07/217,019, filed Jul. 8, 1988, now abandoned.

The present invention relates to a pharmaceutical composition comprising a somatostatin analogue, and to its use in the treatment of breast cancer.

Somatostatin is a tetradecapeptide incorporating a cyclic dodecapeptide having the structure:

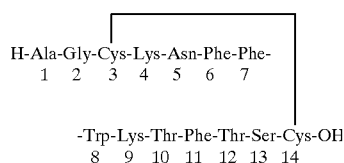

and has the properties of inhibiting the release of growth hormone, inhibiting the release of insulin and glucagon and reducing gastric secretions. Its effect is short and, to solve this problem of short duration, somatostatin analogues which are long acting have been made. These compounds still have to be administered by injection, which can be painful especially in repeated administration.

It has now been found that parenteral compositions of somatostatin analogues, especially octreotide and derivatives thereof, show particularly interesting properties, e.g. they may be better tolerated if lactic acid is present in the pharmaceutical composition.

In a first aspect the present invention provides a pharmaceutical composition comprising a somatostatin analogue and lactic acid.

By the term "analogue" as used herein is meant any straight-chain or cyclic polypeptide derived from that of the naturally occurring tetradecapeptide somatostatin wherein one or more amino acid units have been omitted and/or replaced by one or more other amino radical(s) and/or wherein one or more functional groups have been replaced by one or several other isosteric groups. The term "analogue" includes also the corresponding derivatives bearing a sugar residue. In general, the term covers all modified derivatives of a biologically active peptide which exhibit a qualitatively similar effect to that of the unmodified somatostatin peptide. Hereinafter these compounds are referred to as compounds of the invention.

Cyclic, bridge cyclic and straight-chain somatostatin analogues are known compounds. Such compounds and their preparation are described in U.S. Pat. Nos. 4,310,518 and 4,235,886, in European Patent Specifications EP-A-1295; 70,021; 113,209; 215,171; 203,031; 214,872; 143,307 and in Belgian Patent Specification BE-A-900,089.

When the compounds of the invention bear a sugar residue, this is preferably coupled to a N-terminal amino group and/or to at least one amino group present in a peptide side chain, more preferably to a N-terminal amino group.

Such compounds and their preparation are disclosed e.g. in WO 88/02756.

PREFERRED COMPOUNDS OF THE INVENTION ARE

A. Compounds of formulae I to III

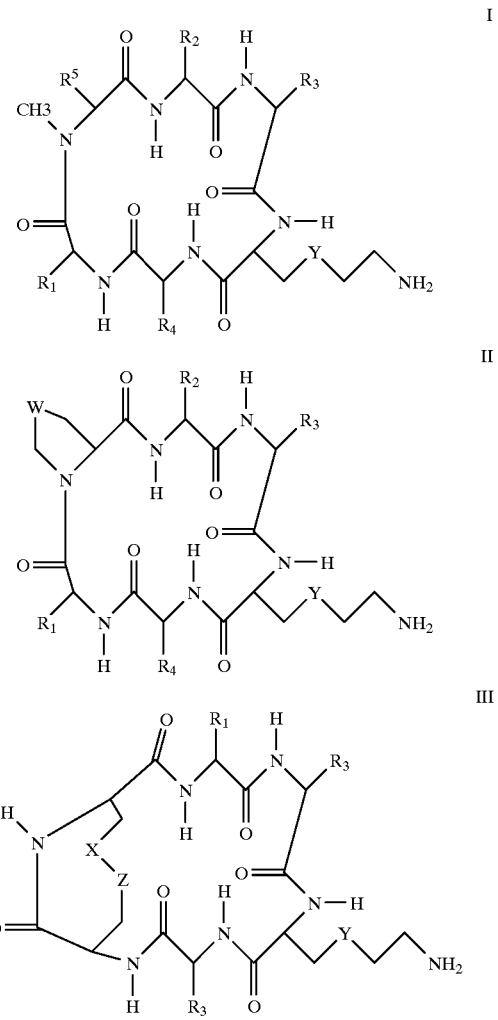

wherein

| | |
|---|---|
| W is | S or $(CH_2)_s$ where s is 0, 1 or 2; |
| one of X and Z | is S and the other is S or $CH_2$; |
| Y is | S or $(CH_2)_t$ where t is 0, 1 or 2; |
| each of $R_1$ and $R_2$ | independently of the other, is $C_{1-5}$ alkyl, benzyl, benzyl having one or two $C_{1-5}$ alkyl, halogen, hydroxy, amino, nitro, and/or $C_{1-5}$ alkoxy substituents, or $C_{1-5}$ alkyl substituted with a 5- or 6- membered heterocyclic ring; |
| $R_3$ is | 3-indolylmethyl, either unsubstituted or having $C_{1-5}$ alkyl, $C_{1-5}$ alkoxy or halogen substitution; |
| $R_4$ is | $C_{1-5}$ alkyl, $C_{1-5}$ hydroxylakyl, benzyl, carboxy-($C_{1-5}$ alkyl), amino ($C_{1-5}$ alkyl) or benzyl having a $C_{1-5}$ alkyl, halogen, hydroxy, amin, nitro and/or $C_{1-5}$ alkoxy substituent; |

| | |
|---|---|
| -continued | |
| $R_5$ is | $C_{1-5}$ alkyl, benzyl, or benzyl having a $C_{1-5}$ alkyl, halogen, hydroxy, amino, nitro, and/or $C_{1-5}$ alkoxy substituent. |

Examples of $C_{1-5}$ alkyl groups are methyl, ethyl, propyl, iso-propyl, butyl, sec-butyl and pentyl; examples of $C_{1-5}$ alkoxy groups are methoxy, ethoxy, propoxy, isopropoxy, butoxy, tert-butoxy, and pentoxy; halogens are fluorine, chlorine, bromine, or iodine: and the term "5- or 6-membered heterocyclic ring" represents such rings with one or two oxygen, nitrogen and/or suphur heteroatoms, e.g. imidazole, furan, thiazole, pyrazole and pyridine.

In the compounds of Formulae I, II and III, there are several asymmetric centres which lead to the existence of optical isomers for such compounds. For each of the asymmetric centres of the various amino acids which make up these cyclic hexapeptides, both the D and L configurations are included.

The following are representative cyclic hexapeptide analogues of somatostatin of Formulae I, II and III:

Ia

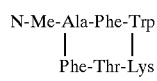
N-Me-Ala-Phe-Trp
|       |
Phe-Thr-Lys

IIa

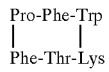
Pro-Phe-Trp
|       |
Phe-Thr-Lys

IIIa

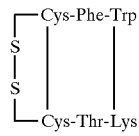

Preferred Formula I compounds are:

1) Cyclo-(N-Me-Ala-Tyr-D-Trp-Lys-Thr-Phe)
2) Cyclo-(N-Me-Ala-Phe-D-Trp-Lys-Thr-Phe)
3) Cyclo-(N-Me-Ala-Phe-L-Trp-Lys-Thr-Phe)
4) Cyclo-(N-Me-Ala-Phe-D-Trp-Lys-Thr-p-Cl-Phe)
5) Cyclo-(N-Me-Ala-Phe-D-5-F-Trp-Lys-Thr-Phe)
6) Cyclo-(N-Me-Ala-Phe-L-5-F-Trp-Lys-Thr-Phe)
7) Cyclo-(N-Me-Ala-Phe-D-Trp-Lys-Ser-Phe)
8) Cyclo-(N-Me-Ala-Tyr-D-Trp-Lys-Val-Phe)
9) Cyclo-(N-Me-Ala-Tyr-D-Trp-Lys-Val-Trp)
10) Cyclo-(N-Me-Ala-Tyr-L-Trp-Lys-Val-Phe)
11) Cyclo-(Ser-Ala-N-Me-Phe-His-D-Trp-Lys)

Preferred Formula II compounds are:

12) Cyclo-(Pro-Tyr-D-Trp-Lys-Thr-Phe)
13) Cyclo-(Pro-Phe-D-Trp-Lys-Thr-Phe)
14) Cyclo-(Pro-Phe-L-Trp-Lys-Thr-Phe)
15) Cyclo-(Pro-Phe-D-Trp-Lys-Thr-p-Cl-Phe)
16) Cyclo-(Pro-Phe-D-5-F-Trp-Lys-Thr-Phe)
17) Cyclo-(Pro-Phe-L-5-F-Trp-Lys-Thr-Phe)
18) Cyclo-(Pro-Phe-D-Trp-Lys-Ser-Phe)

Preferred Formula III compounds are:

19) Cyclo-(Cys-Cys-Tyr-D-Trp-Lys-Thr)
20) Cyclo-(Cys-Cys-Tyr-D-Trp-Lys-Val)
21) Cyclo-(Cys-Cys-Tyr-L-Trp-Lys-Val)
22) Cyclo-(Cys-Cys-Phe-D-Trp-Lys-Thr)
23) Cyclo-(Cys-Cys-Phe-L-Trp-Lys-Thr)
24) Cyclo-(Cys-Cys-His-D-Trp-Lys-Thr)
25) Cyclo-(Cys-Cys-His-D-Trp-Lys-Val)
26) Cyclo-(Cys-Cys-Ala-Phe-D-Trp-Lys-Thr)

B. Compounds of formula IV

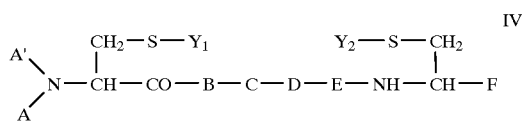

wherein

A is $C_{1-12}$ alkyl, $C_{7-10}$ phenylalkyl or a group of formula RCO—, whereby i) R is hydrogen, $C_{1-11}$ alkyl, phenyl or $C_{7-10}$ phenylalkyl, or ii) RCO— is
 a) an L- or D-phenylalanine residue optionally ring-substituted by F, Cl, Br, $NO_2$, $NH_2$, OH, $C_{1-3}$ alkyl and/or $C_{1-3}$ alkoxy
 b) the residue of a natural α-amino acid other than defined under a) above or of a corresponding D-amino acid, or
 c) a dipeptide residue in which the individual amino acid residues are the same or different and are selected from those defined under a) and/or b) above, the α-amino group of amino acid residues a) and b) and the N-terminal amino group of dipeptide residues c) being optionally mono- or di-$C_{1-12}$ alkylated, A' is hydrogen or, when A is $C_{1-12}$ alkyl or $C_{7-10}$ phenylalkyl, also $C_{1-12}$ alkyl or $C_{7-10}$ phenylalkyl, $Y_1$ and $Y_2$ represent together a direct bond or each of $Y_1$ and $Y_2$ is independently hydrogen or a radical of formulae (1) to (5)

(1)

$$—CO—\underset{\underset{R_b}{|}}{\overset{\overset{R_a}{|}}{C}}—(CH_2)_m—H$$

(2)

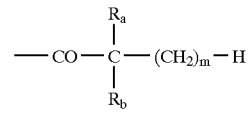

(3)

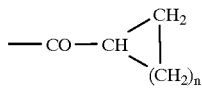

-continued $$—CO—NH—CH(R_d)—COOR_e \quad (4)$$

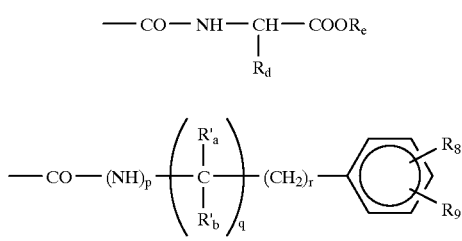
(5)

wherein
- $R_a$ is methyl or ethyl
- $R_b$ is hydrogen, methyl or ethyl
- m is a whole number from 1 to 4
- n is a whole number from 1 to 5
- $R_c$ is $(C_{1-6})$alkyl
- $R_d$ represents the substituent attached to the α-carbon atom of a natural α-amino acid (including hydrogen)
- $R_e$ is $(C_{1-5})$alkyl
- $R_a'$ and $R_b'$ are independently hydrogen, methyl or ethyl,
- $R_8$ and $R_9$ are independently hydrogen, halogen, $(C_{1-3})$ alkyl or $(C_{1-3})$alkoxy,
- p is 0 or 1,
- q is 0 or 1, and
- r is 0, 1 or 2,
- B is -Phe- optionally ring-substituted by halogen, $NO_2$, $NH_2$, OH, $C_{1-3}$alkyl and/or $C_{1-3}$alkoxy, or naphthylalanine
- C is (L)-Trp- or (D)-Trp- optionally α-N-methylated and optionally benzene-ring-substituted by halogen, $NO_2$, $NH_2$, OH, $C_{1-3}$ alkyl and/or $C_{1-3}$ alkoxy,
- D is -Lys-, ThiaLys, γF-Lys, δF-Lys or Orn, optionally α-N-methylated, or a 4-aminocyclohexylAla or 4-aminocyclohexylGly residue
- E is Thr, Ser, Val, Phe, Ile or an aminoisobutyric acid residue
- F is a group of formula $—COOR_7$, $—CH_2OR_{10}$,

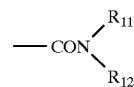

or

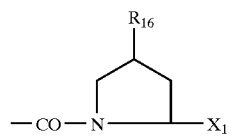

wherein
- $R_7$ is hydrogen or $C_{1-3}$alkyl,
- $R_{10}$ is hydrogen or the residue of a physiologically acceptable, physiologically hydrolysable ester,
- $R_{11}$ is hydrogen, $C_{1-3}$alkyl, phenyl or $C_{7-10}$phenyl-alkyl,
- $R_{12}$ is hydrogen, $C_{1-3}$alkyl or a group of formula $—CH(R_{13})—X_1$,
- $R_{13}$ is $—CH_2OH$, $—(CH_2)_2—OH$, $—(CH_2)_3—OH$, or $—CH(CH_3)OH$ or represents the substituent attached to the α-carbon atom of a natural α-amino acid (including hydrogen) and $X_1$ is a group of formula $—COOR_7$, $—CH_2OR_{10}$ or

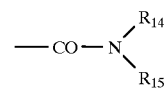

wherein
- $R_7$ and $R_{10}$ have the meanings given above,
- $R_{14}$ is hydrogen or $C_{1-3}$alkyl and
- $R_{15}$ is hydrogen, $C_{1-3}$alkyl, phenyl or $C_{7-10}$phenylalkyl, and
- $R_{16}$ is hydrogen or hydroxy, with the proviso that
when $R_{12}$ is $—CH(R_{13})—X_1$ then $R_{11}$ is hydrogen or methyl, wherein the residues B, D and E have the L-configuration, and the residues in the 2- and 7-position and any residues $Y_1$ 4) and $Y_2$ 4) each independently have the (L)- or (D)-configuration.

In the compounds of formula IV, the following significances or combinations thereof are preferred.

1. A is $C_{7-10}$ phenylalkyl, especially phenethyl, or a group of formula RCO. Preferably A is a group of formula RCO.

1.1. Preferably R is $C_{1-11}$ alkyl or $C_{7-10}$ phenylalkyl, especially $C_{7-10}$ phenylalkyl, more especially phenethyl, or RCO has the meanings a), b) or c).

1.2. When RCO has the meanings a), b) or c), the α-amino group of amino acid residues a) and b) and the N-terminal amino group of dipeptide residues c) is preferably non-alkylated or mono-$C_{1-12}$ alkylated, especially $—C_{1-8}$ alkylated, more especially -methylated. Most preferably the N-terminal is non-alkylated.

1.3. When RCO has the meaning a) this is preferably a') an L- or D-phenylalanine or -tyrosine residue optionally mono-N-$C_{1-12}$ alkylated. More preferably a') is an L- or D-phenylalanine residue or an L- or D-N-($C_{1-8}$-alkyl)-phenylalanine residue. Most preferably a') is a D-phenylalanine or D-N-($C_{1-8}$ alkyl)-phenylalanine residue, especially a D-phenylalanine or D-(N-methyl)-phenylalanine residue.

1.4. When RCO has the meaning b) or c) the defined residue is preferably lipophilic. Preferred residues b) are thus b') α-amino acid residues having a hydrocarbon side chain, e.g. leucine and norleucine residues, said residues having the L- or D-configuration, and preferred residues c) are dipeptide residues in which the individual amino acid residues are the same or different and are selected from those defined under a') and b') above.

1.5. Most preferably RCO has the meaning a) especially the meaning a').

2. B is B', where B' is Phe or Tyr
3. C is C', where C' is -(D)Trp-
4. D is D', where D' is -Lys-, -MeLys- or -Lys(ε-Me)-, especially -Lys-.
5. E is E', where E' is the residue of a natural α-amino acid other than Val, especially -Thr-.
6. F is F', where F' is a group of formula

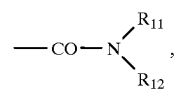

especially a group of

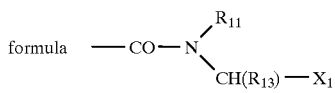

(in which case $R_{11}$=H or $CH_3$). In the latter case the moiety —CH($R_{13}$)—$X_1$ preferably has the L-configuration. Preferably F' is other than -ThrNH$_2$ when E' is Thr.

6.1. $R_{11}$ is preferably hydrogen.

6.2. As the substituent attached to the α-carbon atom of a natural amino acid (i.e. of formula $H_2N$—CH($R_{13}$)—COOH), $R_{13}$ is preferably —$CH_2OH$, —$CH(CH_3)$—OH, isobutyl or benzyl, or $R_{13}$ is —$(CH_2)_2$—OH or —$(CH_2)_3$—OH. It is especially —$CH_2OH$ or —$CH(CH_3)OH$.

6.3. $X_1$ is preferably a group of formula

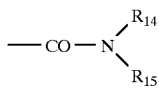

or —$CH_2$—$OR_{10}$, especially of formula —$CH_2$—$OR_{10}$ and $R_{10}$ is preferably hydrogen or has the meaning given under 7 below. Most preferably it is hydrogen.

7. As the residue of a physiologically acceptable, physiologically hydrolysable ester $R_{10}$ is preferably HCO, $C_{2-12}$ alkylcarbonyl, $C_{8-12}$ phenylalkylcarbonyl or benzoyl.

8. Preferably the residues in the 2- and 7-positions have the L-configuration.

9. Preferably $Y_1$ and $Y_2$ together represent a direct bond.

Most preferred compound of formula IV is the compound IVa

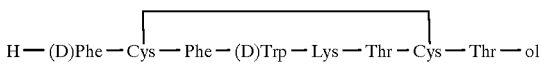

also known as octreotide.

C. Compounds of formulae V to VIII

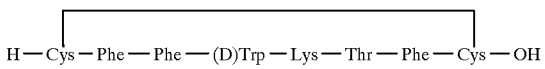

[see Vale et al., Metabolism, 27, Supp. 1, 139, (1978)]

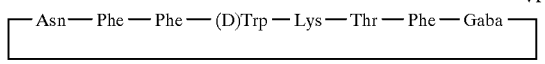

[see European Patent Publication No 1295 and Application No. 78 100 994.9]

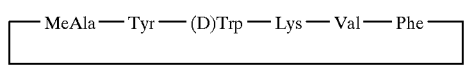

[see Veber et al., Life Sciences, 34, 1371–1378 (1984) and European Patent Application No. 82106205.6 (published as No. 70 021)] also known as cyclo (N-Me-Ala-Tyr-D-Trp-Lys-Val-Phe).

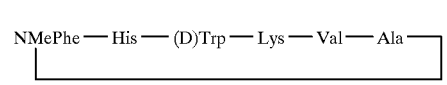

[see R. F. Nutt et al. Klin. Wochenschr. (1986) 64 (Suppl. VII) 71–73.

The contents of all the above publications including the specific compounds are specifically incorporated herein by reference.

The compounds of the invention may exist e.g. in free form, salt form or in the form of complexes thereof. Acid addition salts may be formed with e.g. organic acids, polymeric acids and inorganic acids. Such acid addition salt forms include e.g. the hydrochlorides and acetates. Complexes are e.g. formed from compounds of the invention on addition of inorganic substances, e.g. inorganic salts or hydroxides such as Ca- and Zn-salts, and/or an addition of polymeric organic substances.

The compounds of the invention may be prepared in accordance with conventional methods. They are conveniently used in the form of an acetate hydrate. Typical peptide concentrations are from 85 to 95 percent.

According to the invention, in addition to the lactic acid and the compound of the invention, the pharmaceutical composition preferably contains also a basic compound selected in such a way that the pharmaceutical composition is buffered to a pH of 4 to 4.5, preferably 4.2.

Preferably the basic compound is selected from sodium hydroxide and sodium hydrogen-carbonate. Such a compound is preferably added in such an amount that the resulting pharmaceutical composition has a pH buffered as indicated above.

Preferably the pharmaceutical composition of the invention is water based. It may be used in the same way as for known compositions based on e.g. acetic acid and sodium acetate. Conveniently it is used for parenteral administration, e.g. subcutaneously. Typical doses for s.c. administration are from 0.05 to 1 mg compound of the invention per ml, particularly 0.1 to 1 mg/ml, preferably given twice or once a day or by continous infusion. The composition may be administered at the same doses and in the same way as for other known compositions containing the same active agent.

The ratio of lactic acid to compound of the invention is preferably from about 1:1 to about 40:1, particularly 5:1 to 40:1. The lactic acid is conveniently used as a hydrate, e.g. 88% pure.

Typically the pharmaceutical composition of the invention may contain per ml from 0.05 to 1 mg of a compound of the invention, from about 2 to 4 mg lactic acid, particularly as a hydrate (88% pure), sufficient sodium hydrogen-carbonate or sodium hydroxide to pH 4.2 and sterile water.

The composition of the invention may contain further ingredients, e.g. a preserving agent, for example phenol, and/or an agent for adjusting isotonicity, for example mannitol or sodium chloride. Preferably, phenol is added to the composition when it is formulated as multidose vials.

When mannitol is used for adjusting the isotonicity of the pharmaceutical composition of the invention, the amount of mannitol preferably does not exceed 5.5% by weight of the composition. Conveniently mannitol is present in a ratio mannitol to lactic acid of about 10:1 to 20:1.

When sodium chloride is used for adjusting the isotonicity, it is preferably present in a ratio to lactic acid of about 1:1 to 20:1, more preferably 2:1 to 10:1.

The composition of the invention may be produced according to conventional methods, e.g. by mixing a somatostatin analogue with lactic acid and optionally the other ingredients as mentioned in the desired amount. Preferably the somatostatin analogue is first dissolved in water (for injection). The composition of the invention is advantageously prepared under sterile and aseptic conditions; the compounds of the invention may also be produced under sterile conditions. The composition of the invention being intended for parenteral administration, particularly for injections, it is conveniently filled up in ampoules or vials under aseptic conditions. The pharmaceutical composition may be packed under carbon dioxide or other inert gas to prevent degradation, preferably under carbon dioxide.

After injection, the composition of the invention is locally much better tolerated than one containing acetic acid and sodium acetate, e.g. known compositions of the compound IVa. Particularly the parenteral administration of a composition of the invention, e.g subcutaneous injection, is less painful.

In addition to the improved local tolerance after injection, the composition of the invention which basically contains a polypeptide as somatostatin analogue, exhibits good stability characteristics.

The pharmaceutical composition of the invention is particularly indicated for use in the treatment of breast cancer.

Breast carcinoma is the most common type of tumours in women over 40 years age and a leading cause of deaths. The invention may be of value for tumours which are hormone-dependent, e.g. estrogen-dependent, or hormone-independent. Breast cancer is a disease for which an important effort has still to be invested to find any sort of alleviation.

It has been found that the compounds of formulae I to III, the compounds of formula IV wherein B is B', C is C', D is D', E is E' and F is F', especially the compound IVa, and their derivatives bearing a sugar residue, particularly the derivatives preparable by an Amadori or Heyns rearrangement from a natural or a synthetically accessible mono-, di- or oligosaccharide, and the compounds of formulae V to VIII, as defined above, have a beneficial effect on patients with breast cancer, e.g. in arresting progress of the disease, as indicated by e.g. extent and duration of the response.

Preferred somatostatin analogues bearing a sugar residue are those disclosed in WO 88/02756, the contents of which being incorporated herein by reference.

A particularly preferred compound is

A second clinical trial may be effected as follows:

In a second trial the compounds of the invention are administered to at least 14 patients having breast cancer and the extent and duration of the response determined.

Patients are included who have breast cancer as evidenced by histological biopsy (glandular analysis—EOA). They present a metastatic illness and/or loco-regional localisation which is measurable and evaluable. If desired patients are included who are resistant to other treatment to conventional therapy such as surgery, radiotherapy, other chemotherapy and/or hormone therapy.

The patients present at least one target, on X-ray analysis, which is measurable or evaluable such as a primitive metastatic tumour which is cutaneous or sub-cutaneous. It may be gangliar or visceral. Preferably the patients have lesions which have progressed within the month preceding the trial and have an estimated survival time of at least 3 month. Preferably the trial excludes:

patients in which the sole criteria for diagnosing breast cancer are biological modifications, patients administered with an embroynic carcinoma antigen pathology, patients with ascitis, a pleural effusion, a pulmonary carcinoma lymphangitis, or an osseous localisation as sole metastatic manifestation, patients treated on a unique tumoural target by radiotherapy less than eight weeks before inclusion in the study (they are eligible however if evidence of progression during this time), patients with a unique cerebral localisation, patients presenting another malignant tumour with the exception of a carcinoma in situ in the cervix uteri or a spino- or basocellular skin cancer, and patients not able to attend regular consultations.

With these exclusions the efficacy of the compounds may be followed more clearly. The compounds may be used in the method of treatment at the invention however in treating patients falling in the above exclusion.

The compounds of the invention may be administered at the same dosage as or at a lower dosage than in the first trial, but preferably in two doses, one in the morning and one in the evening. The treatment is for at least 3 months or until complete remission. The response may be followed by conventional methodology, e.g. according to IUCC response criteria, e.g. progression, stabilization, partial or complete remission. The evaluation is effected e.g. on day 0, 15, 45, 60 and 90.

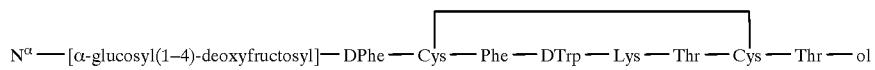

$N^\alpha$ —— [α-glucosyl(1–4)-deoxyfructosyl]—DPhe—Cys—Phe—DTrp—Lys—Thr—Cys—Thr—ol (referred to as compound IVb).

The beneficial effect on patients with breast cancer with the somatostatin analogues as mentioned above may be shown in the following clinical trials:

In a first clinical trial, 5 patients suffering from metastatic breast carcinoma are studied, who had no previous systemic treatment of metastasis (adjuvant treatment is ignored) and had easy access to their veins. The patients had PS 0 or 1 and could be post-menopausal.

The compounds of the invention may be continuously administered parenterally, e.g. s.c. by means of a pump at the rate of e.g. 0.5 to 2 mg per 24 hours, over at least 3 days.

The growth factor IGF profile is determined and the levels found to be reduced.

A third clinical trial may be effected as follows:

Patients with advanced breast cancer are included. In addition their breast cancers are analysed with autoradiography on adjacent tissue sections using as radioligand e.g. either $^{125}$I-[Leu$^8$, D-Trp$^{22}$, Tyr$^{25}$]-somatostatin-28 or a $^{125}$I-Tyr$^3$ analogue of the compound IVa, for their content in somatostatin receptors. The patients have progressive disease and measurable and/or evaluable parameters according to criteria of the IUCC (i.e. appearance of new lesions or growth of existing metastatic lesions) not responding to primary hormonal and/or cytotoxic therapy. As in the above indicated second clinical trial, the third trial preferably also excludes patients with previous or concurrent malignancies at other sites, with the exception of cone biopsied in situ carcinoma of the cervix uteri and adequately treated basal or squamous cell carcinoma of the skin.

The compounds of the invention may be administered at the same dosage as or at a lower dosage than in the second trial. Preferably the compounds of the invention are administered parenterally, e.g. subcutaneous, particularly in a continuous subcutaneous way by means of a portable syringe pump (infusion pump). Treatment is for at least 2 months or until complete remission. The response may be followed by conventional methodology e.g. according to IUCC response criteria. The evaluation is effected e.g. on day 0, 30 and 60. All lesions are measured at each assessment or when multiple lesions are present, a representative number of 5 lesions may be selected for measurement. Regression of the lesions is the sum of the products of the diameters of each individual lesion or those selected for study, which decreases by 50% or more.

The compounds of the invention, e.g. octreotide, is administered, e.g. parenterally, e.g. sub-cutaneously, or orally. The appropriate dosage will vary depending upon, for example, the somatostatin analogue employed, the host, the mode of administration and the severity of the condition being treated. Doses may be in the range used to treat gastro-enteropancreatic endocrine (GI) tumours such as vipomas, or acromegaly, to about 10 times that dose. Preferred ranges are e.g. from about 4 to 10 times the GI-tumour or acromegaly dose.

Thus for octreotide, GI tumours may be treated initially with 0.05 mg once or twice a day by sub-cutaneous injection. Dosage can be increased to 0.2 mg three times daily. For acromegaly daily doses of from 100 to 300 μg s.c. may be used. Octreotide is tolerated at least to 1 mg.

Indicated daily doses for octreotide in the use of the invention are from 0.1 to 1 mg s.c., preferably 0.2 to 1 mg s.c.. Octreotide is preferably administered parenterally in the form of a formulation based on lactic acid as disclosed above. The compound IVb (octreotide with a sugar residue) is preferably administered in an oral form, e.g. at a dosage of 2 μg to 20 mg p.o., preferably 300 to 5000 μg p.o.. Oral unit dosages may contain for example from about 0.5 μg to about 10 mg of compound IVb.

Preferably a dopamine agonist is also administered in the treatment of breast cancer. The preferred dopamine agonist is bromocriptine, preferably used as the mesylate.

Further examples include:

N,N-diethyl-N'-[(3α-4aα,10aβ)-1,2,3,4,4a,5,10,10a-octahydro-6-hydroxyl-1-propyl-3-benzo[quinolinyl] sulfamide, also known as CV, preferably used as the hydrochloride.

Preferred compounds are low molecular weight ergot derivatives, i.e. compounds which do not have a peptide moiety in the 8 position, i.e. not ergopeptides. They may have for example an amino group, e.g. an acylamino, ureidio or sulphamino moiety or thiomethyl moiety in the 8 position which may be substituted by for example one or if desired two (C$_{1-4}$)alkyl groups. Conveniently these have a single bond in the 9,10 position of the ergoline nucleus.

The preferred compounds are 8α-sulphamoylamino ergolines. These may be based on the formula:

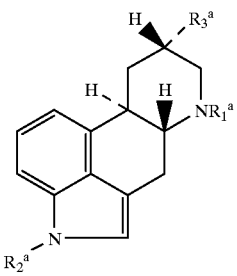

wherein

R$_1{}^a$ inter alia is (C$_{1-4}$)alkyl,

R$_2{}^a$ inter alia is H or (C$_{1-4}$)alkyl,

R$_3{}^a$ inter alia is —NHSO$_2$N[(C$_{1-4}$)alkyl]$_2$

The preferred Examples include:

a) 1,6-dimethyl-8α-(N,N-dimethylsulphamoylamino)-ergoline-I (also known as Mesulergine hereinafter compound B);

b) 6-n-propyl-8α-(N,N-diethylsulphamoylamino)-ergoline-I (N,N-diethyl-N'-(6-propylergolin-8α-yl)sulfamide) preferably used as the hydrochloride, also known as CQP, (hereinafter compound C).

c) N,N-diethyl-N'-[(8α)-1-ethyl-6-methyl-ergolin-8-yl] sulfamide preferably used as the hydrochloride, (hereinafter compound D).

The most preferred example is (b), i.e. compound C.

Other preferred compounds include:

i) 3-(9,10-didehydro-6-methyl-ergolin-8α-yl)-1,1-diethyl-urea (also known as Lisuride preferably used as the hydrogen maleate);

ii) 6-n-propyl-8α-methylmercaptomethyl-ergoline-I (also known as Pergolide preferably used as the mesylate);

iii) Transhydrolisuride also known as terguride having the chemical name 3-(6-methyl-ergolin-8α-yl)-1,1-diethyl-urea, published e.g. in DOS 3135305 and 3124714.

iv) 6-n-propyldihydro-lisuride also known as proterguride having the chemical name 3-(6-n-propyl-ergolin-8α-yl)-1,1-diethyl-urea.

v) 6- and 2-substituted, e.g. 6-n-propyl and/or 2-methyl or bromo derivatives of terguride, lisuride and proterguride e.g. as published in European Patent Publication No. 21206 (A.1) and 160842 (A.1) the contents of which especially the examples and pharmacological data thereof, are incorporated herein by reference. Examples include 2-bromerguride, also known as 2-bromolisuride, preferably used in the form of the hydrochloride.

vi) Metergoline, also known as (+)-N-(carboxy)-1-methyl-9,10-dihydrolysergamine benzyl ester.

vii) dosergoside, also known as N-(1S,2R,3E)-2-hydroxy-1-(hydroxymethyl)-3-heptadecanyl)-6-methylergoline-8-beta-carboxamide.

viii) FCE-21336 also known as 1-ethyl-3-(3'-dimethylaminopropyl)-3-(6-alkyl-ergoline-8'-beta-carbonyl)-urea preferably used as the diphosphate.

ix) GYKI-32887 also known as 6-methyl-8-(N-mesyl-N-2-azidoethyl) ergolene preferably used as the bimaleate, e.g. as disclosed in U.S. Pat. No. 4,299,836.

Groups of compounds include compounds of formula (I')

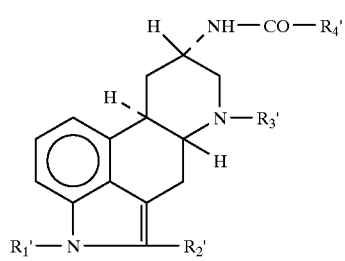

wherein
- $R_1'$ is hydrogen or $C_{1-4}$alkyl,
- $R_2'$ is hydrogen, chlorine, bromine or methyl,
- $R_3'$ is $C_{1-5}$alkyl or $C_{3-5}$alkenyl in which the double bond is not at the carbon atom adjacent to the nitrogen atom, and
- $R_4'$ is $C_{3-7}$alkyl; $C_{3-7}$cycloalkyl; adamantyl; phenyl; phenyl substituted by one or more members selected from the group consisting of $C_{1-3}$alkyl, $C_{1-3}$alkoxy, $C_{1-3}$alkylthio, trifluoromethyl, hydroxy, nitro, amino and mono- and di($C_{1-3}$alkyl)-amino; or phenyl bearing a condensed non-aromatic, heterocyclic ring having 5- or 6-ring members including 1 or 2 hetero atoms selected from the group consisting of oxygen and sulphur, published in GB 2,152,507 A, the contents of which especially the examples and pharmacological data thereof are incorporated herein by reference, e.g. (5R,8S,10R)-2,6-dimethyl-8α-pivaloylamino-ergoline (hereinafter compound E) preferably used as the hydrochloride, and the 2-chloro derivative, (5R,8S,10R)-2-chloro-6-methyl-8α-pivaloylamino-ergoline.

Other examples include a compound of formula I"

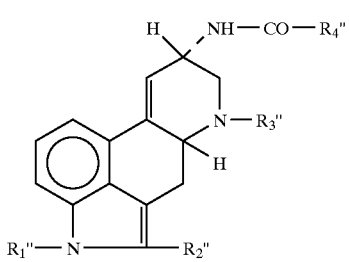

wherein
- $R_1''$ is hydrogen or $C_{1-4}$alkyl,
- $R_2''$ is hydrogen, chlorine,, bromine or methyl,
- $R_3''$ is $C_{1-5}$alkyl or $C_{3-5}$alkenyl in which the double bond is not at the carbon atom adjacent to the nitrogen atom, and
- $R_4''$ is $C_{1-7}$alkyl; $C_{3-7}$cycloalkyl; adamantyl; phenyl; phenyl substituted by one or more members selected from the group consisting of $C_{1-3}$alkyl, $C_{1-3}$alkoxy, $C_{1-3}$alkylthio, trifluoromethy, hydroxy, nitro, amino and mono- and di-($C_{1-3}$alkyl)-amino; or phenyl fused with a non-aromatic, heterocyclic ring having 5- or 6-ring members including 1 or 2 hetero atoms selected from the group consisting of oxygen and/or sulphur, with the proviso that when $R_2''$ is hydrogen, neither $R_3''$ nor $R_4''$ is methyl, e.g. the compounds wherein $R_1''$=H $R_2''$=Br or especially $CH_3''$, $R_3''$=$CH_3$ and $R_4''$=tert butyl, filed off German Application P 3447383.1 filed Dec. 24, 1984 as English application No. 8531420, now published as G.B. Application 2169291 A and also in other countries, the contents of which including all the examples thereof are incorporated herein by reference.

These dopamine agonists may be used for example in free base form or in pharmaceutically acceptable acid addition salt form, e.g. the hydrochloride, maleate or mesylate.

The compounds may be administered in the second clinical trial in association with the compounds of the invention. The compounds are administered at daily doses used to lower prolactin levels. For example bromocriptine is administered at a daily dose of 5 mg p.o. twice a day.

The present invention accordingly in one aspect provides:

a) Use of a somatostatin analogue of formulae I to III, of formula IV wherein B is B', C is C', D is D', E is E', F is F' and A, A', $Y_1$ and $Y_2$ are as defined above, and their derivatives bearing a sugar residue, preferably their derivatives preparable by an Amadori or Heyns rearrangement from a natural or synthetically accessible mono-, di- or oligosaccharide, or of formulae V to VIII in free form or a pharmaceutically acceptable salt form of complex form, in the treatment of breast cancer, e.g. hormone-dependent or hormone-independent breast tumours and/or somatostatin receptor positive breast tumours, and/or b) Use of a somatostatin analogue as mentioned in a) above in the manufacture of a medicament suitable for the treatment of breast cancer, particularly a parenteral or oral composition, e.g. a composition for subcutaneous administration, and/or c) A method of treating breast cancer in a subject which comprises administering a therapeutically effective amount of a somatostatin analogue as mentioned in a) above to a subject in need of such a treatment, and/or d) A method of co-administering a somatosatin analogue as mentioned in a) above and a dopamine agonist in the treatment of breast cancer to a subject in need of such a treatment.

The pharmaceutical compostition of the invention is particularly useful in the treatment of breast cancer when the somatostatin analogue is administered s.c., e.g. by continuous infusion. The administration can be effected continuously over 24 hours with an acceptable tolerance for the patient.

Examples of compositions are as follows:
Somatostatin Concentrations per ml

|  | Ex. 1 | Ex. 2 | Ex. 3. | Ex. 4 |
|---|---|---|---|---|
| 1. Ampoules | | | | |
| A. Octreotide* | 0.05 mg | 0.1 mg | 0.2 mg | 0.5 mg |
| Mannitol | 45.0 mg | 45.0 mg | 45.0 mg | 45.0 mg |
| Lactic acid (88%) | 3.4 mg | 3.4 mg | 3.4 mg | 3.4 mg |
| Sodium hydrogeno-carbonate | to pH 4.2 | to pH 4.2 | to pH 4.2 | to pH 4.2 |
| Water(inject.grade) | to 1 ml | to 1 ml | to 1 ml | to 1 ml |
| Carbon dioxide | q.s. | q.s. | q.s. | q.s. |

|  | Ex. 5 |
|---|---|
| B. Octreotide* | 0.2 mg |
| NaCl | 7.5 mg |
| Lactic acid (88%) | 3.4 mg |
| Sodium hydrogeno- | to pH 4.2 |

| -continued | |
| --- | --- |
| carbonate | |
| Water (injection grade) | to 1 ml |
| Carbon dioxide | q.s. |

Ex. 6

| 2. Vials | |
| --- | --- |
| Octreotide* | 0.2 mg |
| Mannitol | 45.0 mg |
| Lactic acid (88%) | 3.4 mg |
| Phenol | 5.0 mg |
| Sodium hydrogeno-carbonate | to pH 4.2 |
| Water (injection grade) | to 1 ml |
| Carbon dioxide | q.s. |

*given as the acetate peptide content 87 per cent.

The compositions are prepared by standard techniques, e.g. in charges of 50 liters to provide about 43 000 ampoules of 1 ml or 8400 vials under carbon dioxide gassing. The compositions are filtered (e.g. through 0.2 micron holes at 0.5 bar) and introduced in the ampoules or vials under aseptic conditions.

What is claimed is:

1. A method of treating breast cancer in a subject which comprises administering a therapeutically effective amount of octreotide or octreotide as a pharmaceutically acceptable salt to a subject in need of such treatment.

2. A method of claim 1 in which the octreotide is co-administered with a dopamine agonist.

* * * * *